United States Patent [19]

Bestwick et al.

[11] Patent Number: 5,366,954
[45] Date of Patent: Nov. 22, 1994

[54] FLORAL PRESERVATIVE COMPRISING 5-DEOXY-5-ETHYLTHIO-D-RIBOSE AND METHOD OF USE

[75] Inventors: Richard K. Bestwick, Portland; Vijaya K. Mokkapati, Beaverton; Adolph J. Ferro, Lake Oswego, all of Oreg.

[73] Assignee: Epitope, Inc., Beaverton, Oreg.

[21] Appl. No.: 944,916

[22] Filed: Sep. 15, 1992

[51] Int. Cl.$^5$ ............................................. A01N 3/02
[52] U.S. Cl. .................................................. 504/114
[58] Field of Search ................... 504/114; A01N 3/02

[56] References Cited

U.S. PATENT DOCUMENTS 4,820,692  4/1989  Risco et al. ................... 536/18.4

OTHER PUBLICATIONS

MacMillan, J. *Harmond Regulation of Development.* "4.1.6–Ethylene" pp. 317–336. N.Y.: Springer–Verlag. 1980.

Miyazaki et al. *Phytochemistry* 26:10. "Inhibition of the Methionine Cycle Enzymes". pp. 2655–2660. 1987.

Kushad, M. M., et al., "5'–Methylthioadenosine Nucleosidase and 5–Methylthioribose Kinase Activities and Ethylene Production during Tomato Fruit Development and Ripening," Plant Physiol. 79:525–529 (1985).

Myers, R. W., and Abeles, R. H. "Conversion of 5–S–Ethyl–5–thio–D–ribose to Ethionine in *Klebsiella pneumoniae,*" J. Biol. Chem. 264(18):15047–10551 (1989).

Riscoe, M. K., et al., "Analogs of 5–Methylthioribose, a Novel Class of Antiprotozoal Agents," Antimicrobial Agents and Chemotherapy 32(12):1904–1906 (1988).

Riscoe, M. K., et al., "Methionine Recycling as a Target for Antiprotozoal Drug Development," Parasitology Today 5:330–333 1989.

Primary Examiner—Glennon H. Hollrah
Assistant Examiner—S. Mark Clardy
Attorney, Agent, or Firm—Vincent M. Powers; Gary R. Fabian; Peter J. Dehlinger

[57] ABSTRACT

The present invention includes a method of extending bloom life of a cut flower. In the method, a storage solution containing 5-deoxy-5-ethylthio-D-ribose (ETR) is provided, and the stem of the cut flower is bathed in the solution. ETR is safe for human use, and is effective at relatively low concentrations. A method for synthesizing 5-deoxy-5-alkylthioribose compounds is also disclosed.

5 Claims, 5 Drawing Sheets

FLORAL PRESERVATIVE COMPRISING 5-DEOXY-5-ETHYLTHIO-D-RIBOSE AND METHOD OF USE

FIELD OF THE INVENTION

The present invention relates to floral preservatives, and in particular, to use of an analog of 5-deoxy-5-methylthio-D-ribose to extend the bloom life of cut flowers.

REFERENCES

Baker, J. E., Wang, C. Y., Lieberman, M., and Hardenburg, R. (1977) *Hort. Science* 12: 38–39.

Beyer, E. M., Jr. (1976) *Plant Physiol.* 58: 268–271.

Fujino, D. W., Reid, M. S., and Yang, S. F. (1981) *Acta Hortic.* 113: 59–64.

Imasaki, H. (1991) "The Biochemistry of Ethylene Biosynthesis", A. K. Mattoo and J. C. Suttle, Eds., CRC Press, Boca Raton, Fla., pp. 1–20.

Myers, W. R., and Abeles, R. H. (1989) *J. Biol. Chem.* 264: 10547–10551.

Reid, M. S., and Wu, M. J. (1991) "Ethylene in Flower Development and Senescence", in *The Plant Hormone Ethylene*, A. K. Mattoo and J. C. Suttle, Eds., CRC Press, Boca Raton, Fla., pp. 215–234.

Riscoe, M. K., Ferro, A. J., and Fitchen, J. H. (1988) *Antimicrob. Agents Chemother.* 32: 1904–1906.

Riscoe, M. K., Ferro, A. J., and Fitchen, J. H. (1989) *Parasitology Today* 5: 330–333.

Sisler, E. C., Reid, M. S., and Fujino, D. W., (1983) *Acta Hortic.* 141: 229–234.

Ward, T. M., Wright, M., Roberts, J. A., Self, R., and Osborne, D. J. (1978) "Analytical Procedures for the Assay and Identification of Ethylene" in *Isolation of Plant Growth Substances*, J. R. Hillman, Ed., Cambridge University Press, Cambridge.

BACKGROUND OF THE INVENTION

The onset of senescence is a significant problem in the flower industry. Although the useful lifetime of cut flowers can be extended by refrigeration and by use of certain chemical preservatives, the fact that many flower varieties are shipped as cut flowers over long distances has provided strong motivation to develop additional means to extend flower bloom life.

Although placing cut flowers in a solution of water affords some measure of preservation by keeping the flowers hydrated, chemical preservatives are often added to such a solution to extend bloom life. Among the chemical preservatives currently in use are nutrient supplements, which may include a sugar component as well as an acidic agent to maintain the pH of the solution at about 4. Nutrient supplements of this type are commercially available, and include "CRYSAL" and "FLORALIFE", for example.

Other chemical preservatives currently in use work by interfering with the action of ethylene, which plays a central role in senescence. Such preservatives include silver thiosulfate (STS), 2,5-norbornadiene, aminooxyacetic acid (AOA), and aminoethyoxyvinylglycine (AVG). Silver thiosulfate and 2,5-norbornadiene act by antagonistically blocking ethylene action. Aminooxyacetic acid and aminoethyoxyvinylglycine, on the other hand, act by inhibiting ethylene synthesis. Although these agents have been shown to be effective floral preservatives (Reid et al., 1991; Beyer, 1976; Sisler, 1983; Fujino et al., 1981; Baker et al., 1977) and, moreover, are sometimes effective when used in combination with a nutrient supplement such as mentioned above, their toxicity and expense present significant drawbacks. Accordingly, new post-harvest floral preservatives that are non-toxic and environmentally safe have been sought.

SUMMARY OF THE INVENTION

The present invention includes, in one aspect, a method of extending bloom life of a cut flower. In the method, a storage solution containing 5-deoxy-5-ethylthio-D-ribose (ETR) is provided, and the stem of the cut flower is bathed in the solution. Use of ETR can extend the bloom life of carnations and roses by several days. ETR is safe for human use, and is effective at relatively low concentrations.

In another aspect, the present invention includes a new method for synthesizing 5-deoxy-5-alkylthioribose compounds. The method includes, in a first step, treating methyl 2,3-O-isopropylidene-5-O-p-toluenesulfonyl-$\beta$-ribofuranoside with an alkanethiol in methanolic sodium methoxide to produce a methyl 5-deoxy-5-alkylthio-2,3-O-isopropylidene-$\beta$-ribofuranoside, where the alkanethiol is a $C_1$–$C_4$ linear or branched-chain alkanethiol. In a second step, the methyl 5-deoxy-5-alkylthio-2,3-O-isopropylidene-$\beta$-ribofuranoside is hydrolyzed to produce 5-deoxy-5-alkylthioribose. When the alkanethiol is ethanethiol, the method produces 5-deoxy-5-ethylthioribose in high yield.

DETAILED DESCRIPTION OF THE INVENTION

A. Definitions

The terms defined in this section have the following meanings unless otherwise indicated.

The abbreviations "MTR" and "ETR" denote 5-deoxy-5-methylthio-D-ribose and 5-deoxy-5-ethylthio-D-ribose, respectively. "Ethylthioribose" and "5-ethylthioribose" denote 5-deoxy-5-ethylthioribose, without specification of the enantiomeric composition (D, L, or a D,L mixture).

The "bloom life" of a flower is the time during which a flower shows an acceptable bloom. The time period, usually measured in days, is defined as beginning when the flower is cut at the stem ("harvested") from a living plant, and ending on the last day the flower shows an acceptable bloom. The definition of an acceptable bloom varies according to flower variety, but is generally defined as a bloom not showing signs of senescence. For carnations, signs of senescence include the appearance of brown petal tips or inrolling of petals. For roses, signs of senescence include the appearance of a bent neck, wilted petals, or blackening of the petal tips. When bloom life is reported collectively for a group of flowers, the reported value is the average of the bloom lives of the individual flowers in the group, plus or minus a standard deviation.

"Live bloom fraction" is the fraction of a group of flowers still having acceptable blooms.

B. Synthesis of 5-deoxy-5-(ethylthio)ribose (ETR)

The present invention includes, in one aspect, an improved synthetic scheme for the preparation of 5-ethylthioribose and related derivatives. The synthetic scheme disclosed herein is more economical than previous approaches, and provides 5-ethylthio-D-ribose (ETR) from methyl 2,3-O-isopropylidine-5-O-p-toluenesulfonyl-$\beta$-D-ribofuranoside, or if preferred, methyl 2,3-O-isopropylidine-$\beta$-D-ribofuranoside or D-ribose, as a starting material. Previous approaches, such as that described in U.S. Pat. No. 4,820,962, have relied on adenosine as a starting material.

Figure 1:
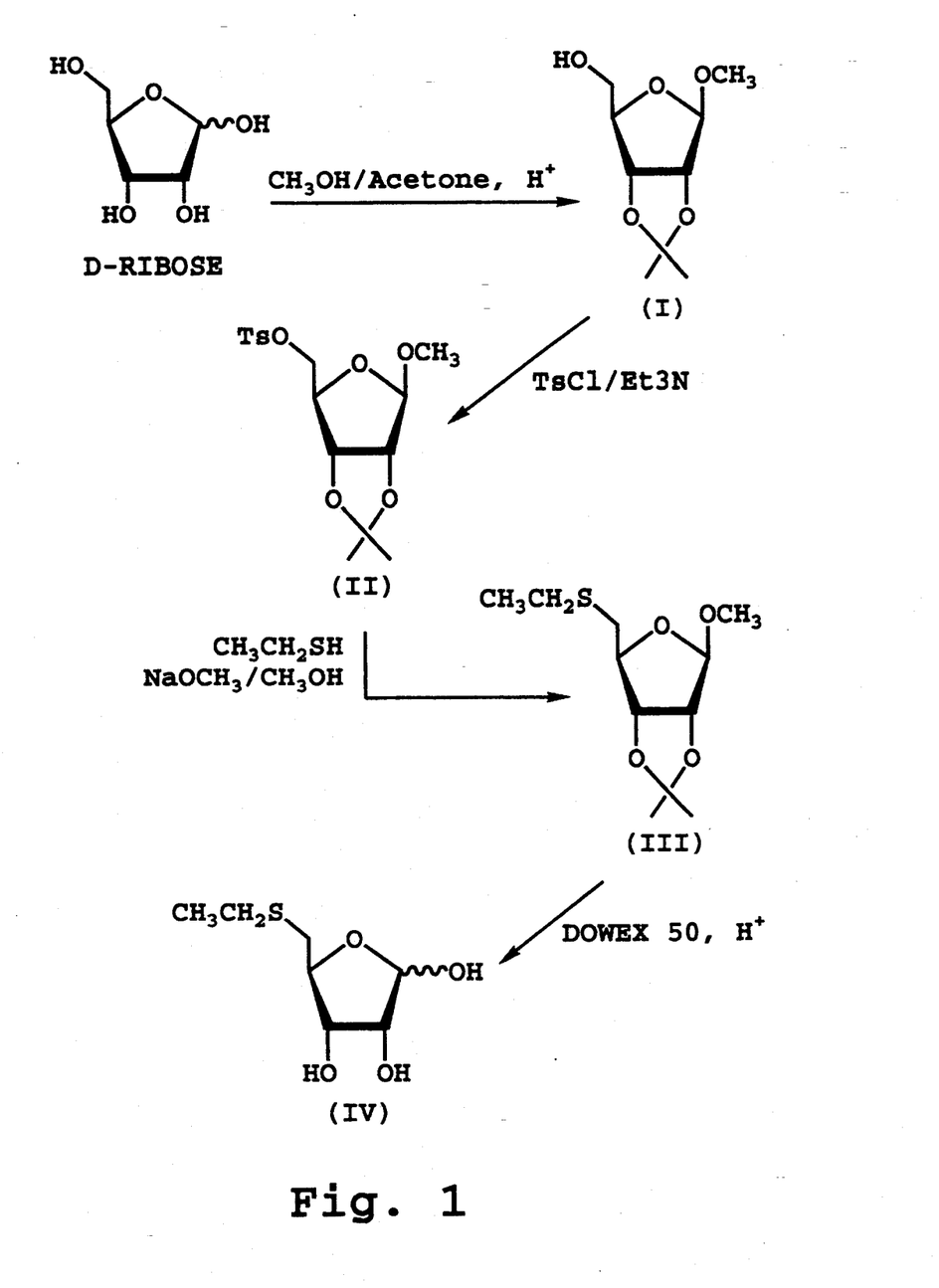
FIG. 1 shows a synthetic reaction scheme for producing 5-ethylthioribose.

A general scheme for preparing ETR according to the present invention is illustrated in FIG. 1. Starting with D-ribose, the 1-, 2-, and 3-hydroxyl groups are simultaneously protected in an acidic methanol-acetone solution by conversion of the 1-hydroxyl group to a methoxy group and by reaction of the 2- and 3-hydroxyl groups with acetone to form the 2,3-O-isopropylidene adduct I. The 5-hydroxyl group of I is then tosylated using tosyl chloride (p-toluenesulfonyl chloride), giving tosylate II. The resultant tosylate is reacted with ethanethiol in methanolic sodium methoxide, thereby producing a 5-deoxy-5-ethylthio-D-ribose derivative III. In a final step, the hydroxyl protecting groups are removed by hydrolysis. While hydrolysis under acid conditions can be used, for example, hydrolysis using Dowex-50-X2 (100-200 mesh) is particularly effective, producing ETR (IV) in nearly quantitative yield. Details of the above reactions are given in Example 1.

The reactions described above can be used to prepare ETR in 4 steps from D-ribose as the starting material. However, it can be appreciated that where intermediate I or II is commercially available, the reaction scheme can be abridged to synthesize ETR (or a related alkylthioribose compound) from the commercially available intermediate. Moreover, it can be appreciated that the above reactions can be adapted to produce a variety of 5-deoxy-5-alkylthioribose compounds, where the alkyl groups include linear or branched chains having one to four carbons. In addition, L-ribose compounds can be analogously prepared by the reactions above by use of L-ribose derivatives in place of D-ribose derivatives.

C. Use of ETR as a Floral Preservative

In accordance with another aspect of the invention, a method is provided for extending bloom life of a cut flower. In the method, a storage solution containing 5-deoxy-5-ethylthio-D-ribose (ETR) is provided, and the stem of a cut flower is bathed in the solution.

The concentration range of ETR that is effective for extending bloom life varies according to flower variety. In general, the effective range is between about 0.01 and 10 mM, and preferably about 0.1 mM to 5 mM. A concentration of between about 1 and 5 mM ETR has been found to be most effective for extending the bloom life of carnations, whereas somewhat lower concentrations, between about 0.1 and 1 mM ETR, have been found to be effective for roses. Best results are obtained when the flower is placed in the ETR-containing solution immediately after harvest, typically at room temperature or below, and for a period of several hours, e.g., about 3 hours, to a day or more, e.g., throughout the bloom life of the cut flower.

The mode by which ETR increases bloom life may involve interference of ethylene synthesis by ETR via the methionine recycling pathway found generally in plants (Imasaki, 1991). The step in the pathway at which such interference may occur, if indeed ETR is acting at this level, is not known. However, it should be noted that an advantage of ETR as a floral preservative is that ETR is not toxic to mammalian cells (Riscoe et al., 1988; 1989; Myers and Abeles, 1989).

The efficacy of ETR as a floral preservative has been characterized in studies described below.

In a study to characterize the utility of ETR with carnations, whole, freshly cut carnations (Katia and Vanessa varieties) treated by bathing the stems for 24 hours in a solution of either water alone, 5 mM ETR in water, or an aqueous STS solution such as typically used in the flower industry. The flowers were then removed from the solutions and shipped to the Agritope Laboratories in Beaverton, Oreg., for further testing. Upon arrival, the flowers were cut to about 12 inches in length and were placed in groups of six in a storage solution containing either water alone or 2 mM ETR in water, and the bloom life of each flower was determined. The results are shown in Table 1.

TABLE 1

| Carnation Bloom Life Extension: ETR vs STS | | |
|---|---|---|
| treatment | Katia bloom life (days) | Vanessa bloom life (days) |
| water/water | 9.3 ± 0.8 | 10.8 ± 1.5 |
| STS/water | 11.7 ± 0.8 | 15.7 ± 1.5 |
| 5 mM ETR/water | 12.2 ± 4.0 | 16.7 ± 3.3 |
| water/2 mM ETR | 13.3 ± 2.3 | 12.0 ± 2.3 |
| 5 mM ETR/2 mM ETR | 16.8 ± 1.5 | 14.3 ± 2.1 |

As can be seen from Table 1, water alone afforded bloom lives of 9 and 11 days, respectively, for Katia and Vanessa carnations. Pretreatment with STS, followed by storage in water, increased bloom life over that of a water/water control by about 3 and 5 days, respectively. In samples where ETR was employed, comparable or even longer bloom lives were observed. With the Katia variety, the inclusion of ETR in either the pretreatment solution or the storage solution afforded bloom life values similar to that observed for pretreatment with STS. When ETR was used in both solutions, however, a further enhancement of 3-4 days was observed. With the Vanessa variety, the inclusion of ETR in one or both solutions afforded bloom lives that were from about 1-6 days longer than what water alone provided. Although pretreatment with STS gave a better result than obtained when ETR was included in only one of the solutions, the inclusion of ETR in both the pretreatment solution and the storage solution yielded the longest bloom life observed for this variety.

In summary, although varietal differences are apparent, the results demonstrate that the inclusion of ETR in either or both of the solutions in the above protocol significantly extended the bloom life of the carnations tested, relative to what was obtained with water alone. Furthermore, ETR was comparable in effectiveness to STS with Vanessa carnations and was superior with Katia carnations. In general, ETR was most effective when included in the pretreatment step, immediately after harvest.

To investigate the effect of ETR on ethylene production, Vanessa carnations were subjected to pretreatment and storage solutions as above, except that the pretreatment step was limited to either water or 5 mM ETR in water, and the storage solution (10 ml) was either water or 2 mM ETR in water. Following a waiting period of 7 days (post-harvest), ethylene production was measured daily for each individual flower by sealing each flower in a jar for about an hour to trap any ethylene produced, and then quantitating the ethylene in the jar by gas chromatography of a 2 ml sample. The results for 3 different combinations of pretreatment and storage solutions are shown in FIGS. 2A–2C, which illustrate the timing and magnitude of ethylene production for each flower tested.

Figure 2A:
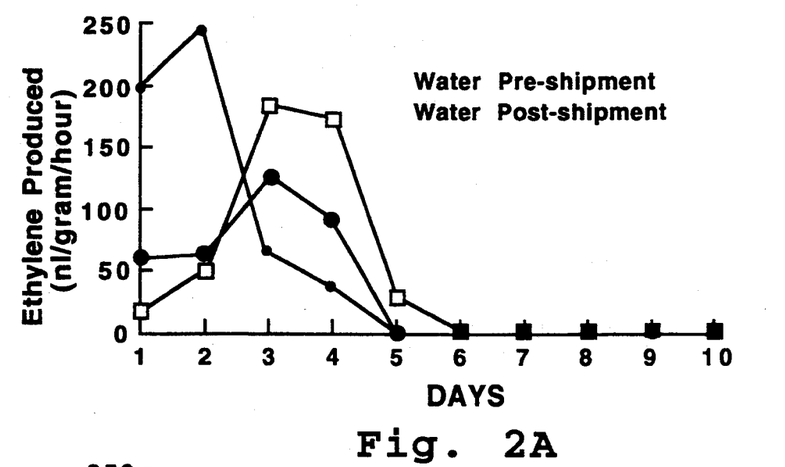
FIGS. 2A–2C show time courses of ethylene production by carnations treated with different levels of 5-deoxy-5-ethylthio-D-ribose.
Figure 2B:
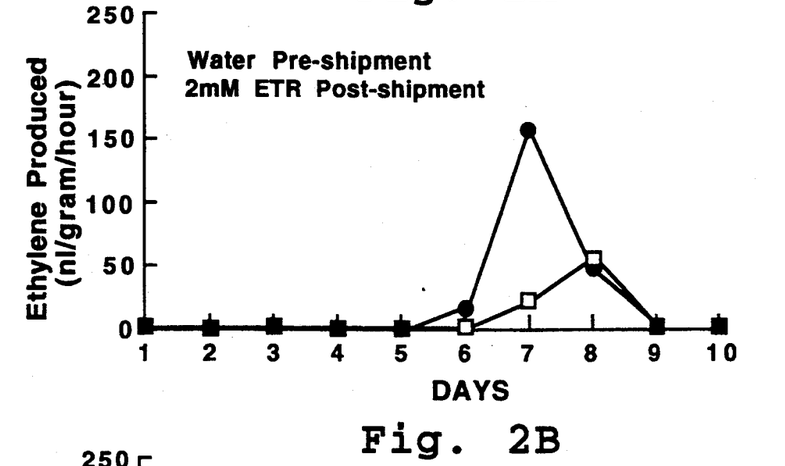
Figure 2C:
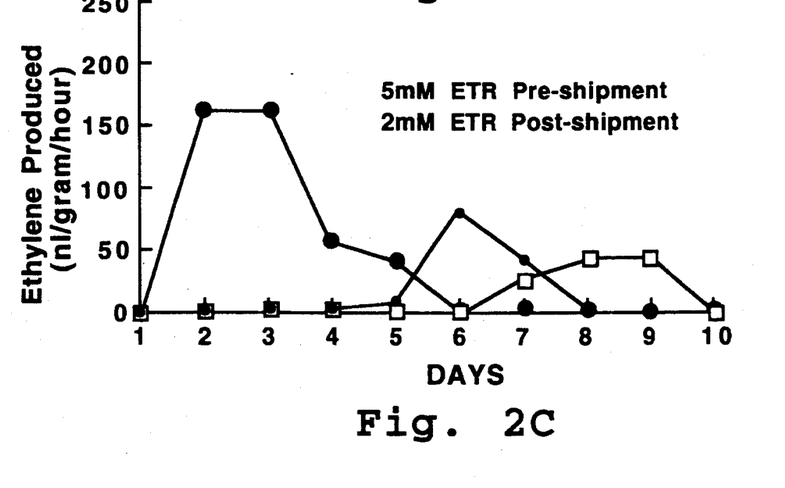

With reference to FIG. 2A, it can be seen that the carnations treated with only water showed maximal ethylene evolution within the first 2 or 3 days of monitoring (9 or 10 days post-harvest), with peak evolution rates of about 250 nl/g/hour. In contrast, the inclusion of ETR in either the storage solution alone or in both the pretreatment and storage solutions (FIGS. 2B and 2C, respectively) significantly delayed the onset of ethylene production and reduced the magnitude of production as well, relative to the water control. One flower in FIG. 2C behaved as though no ETR was present in either solution, an anomaly that reflected the occasional variability seen in the study. Nonetheless, the results show a correlation between the timing and magnitude of ethylene production and the presence or absence of ETR in the pretreatment and/or storage solution. Moreover, the timing of ethylene production was roughly coincident with changes in bloom appearance that were indicative of senescence.

Figure 3:
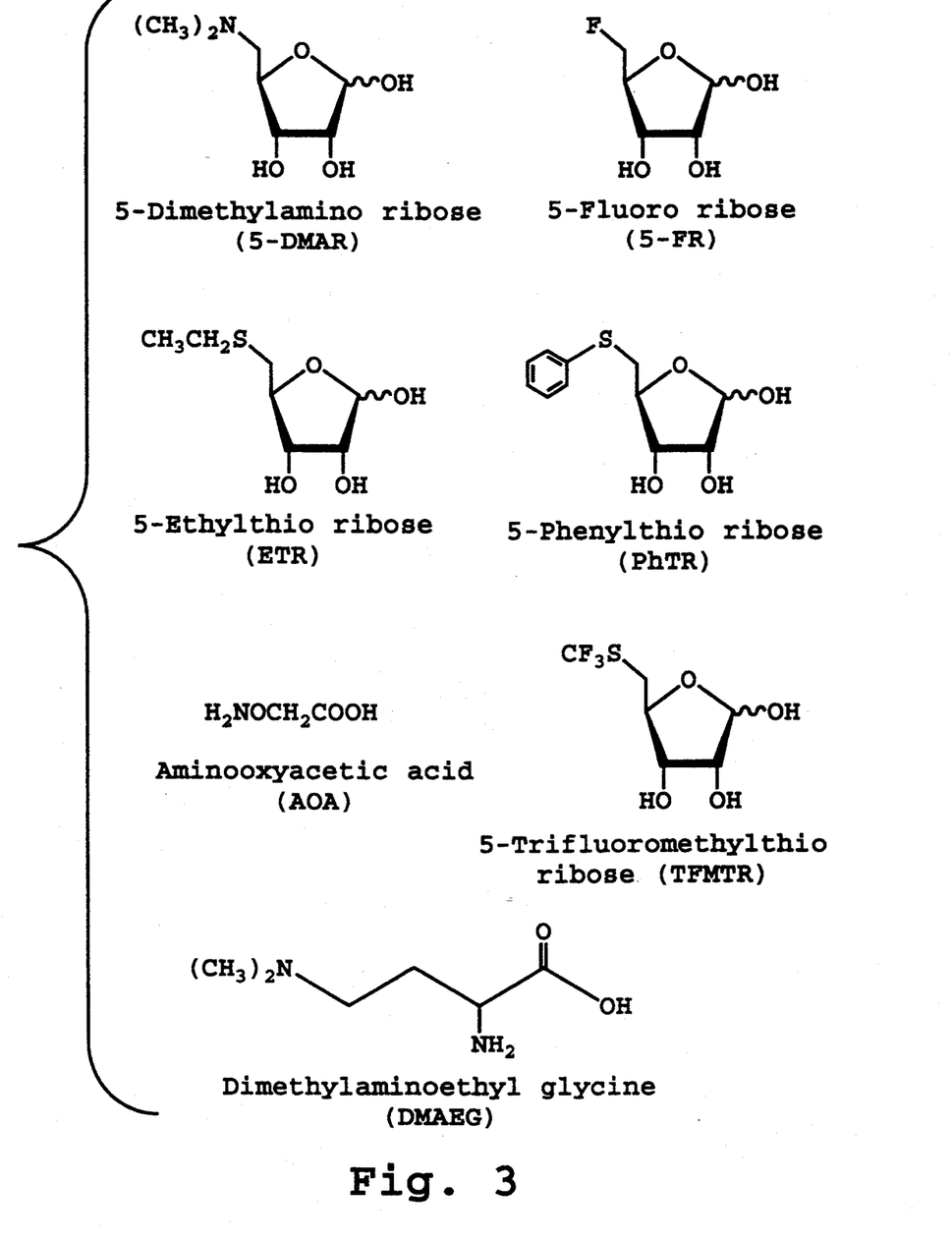
FIG. 3 shows chemical structures of compounds tested for floral preservative activity with carnations in the presence of a nutrient supplement.

To compare the effect of a number of selected compounds on the bloom life of carnations, the compounds shown in FIG. 3 were tested using the protocol described below. The test compounds included the MTR analogs ETR, 5-dimethylaminoribose (5-DMAR), 5-fluororibose (5-FR), 5-phenylthioribose (5-PhTR), and 5-trifluoromethylthioribose (TFMTR), as well as related compounds aminooxyacetic acid (AOA) and dimethylaminoethylglycine (DMAEG). AOA was included in the study as a positive control, since AOA is known to extend the bloom life of carnations (Fujino et al., 1981). DMAEG was tested as a metabolite that could potentially be formed from DMAR via the methionine recycling pathway. Also included in the storage solution was a nutrient supplement (see Example 4) representative of a variety of flower nutrient supplements which are commonly used in cut flower preservation (e.g., Floralife ™, available from Floralife Inc., St. Paul, Minn., and Chrysal ™, available from Pokon and Chrysal, Inc., Miami, Fla.).

Carnations in this study (Nora, Katia, Tanga, and Vanessa varieties) were allowed to stand for 24 hours in a water pretreatment solution immediately after harvest. Following this pretreatment step, the carnations were shipped to the Agritope laboratory in Beaverton, Oreg., by overnight air freight. Upon receipt, the flowers were cut to about 12 inches in length, and three flowers of each variety were immediately placed in a storage solution of (i) water, (ii) a nutrient supplement (see Example 4), or (iii) the nutrient supplement in water additionally containing a 1 mM concentration of one of the compounds shown in FIG. 3. Details of this study are given in Example 4.

Figure 4:
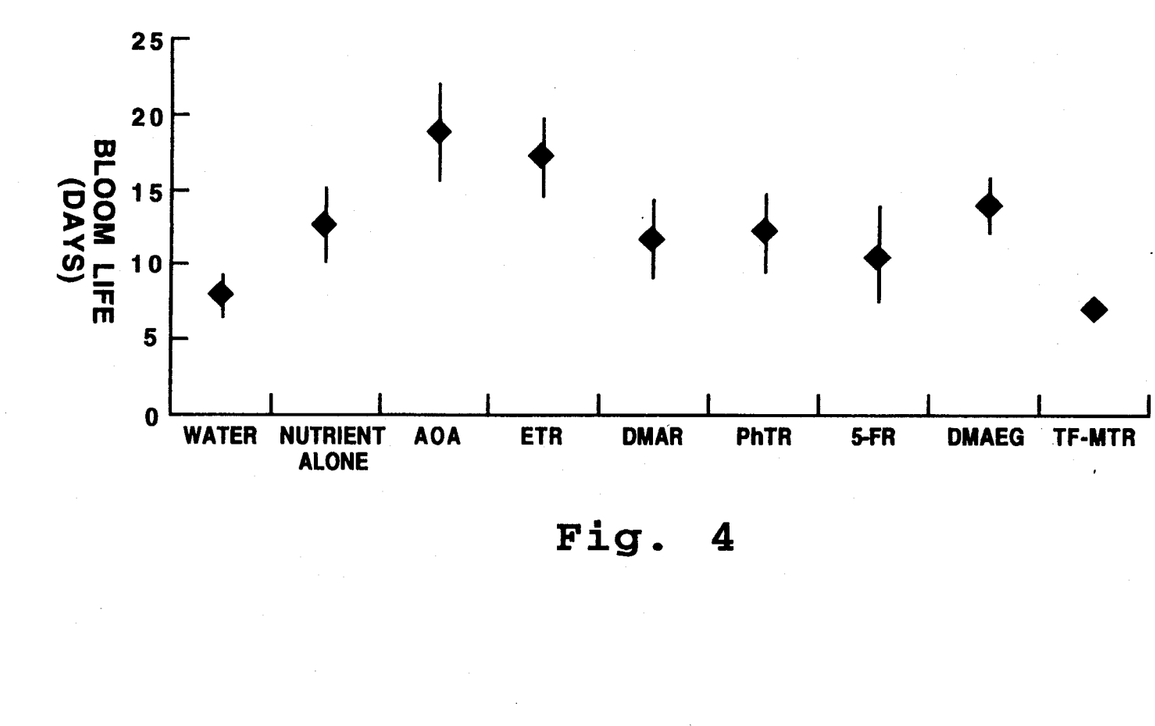
FIG. 4 shows bloom life extensions induced with carnations by the compounds of FIG. 3.

As seen in FIG. 4, which shows the combined results for the four carnation varieties tested, a storage solution of water afforded a bloom life of 8 days, whereas inclusion of the nutrient supplement defined above increased bloom life to about 12 days. When used with the nutrient supplement, both AOA and ETR extended bloom life by about 5–6 days relative to what was obtained with the nutrient supplement alone. In contrast, the compounds DMAR, PhTR, 5-FR, and DMAEG, when used with the nutrient supplement, showed no improvement relative to the nutrient supplement alone. Notably, TFMTR actually counteracted the beneficial effect of the nutrient supplement on bloom life, causing blackening of the petals and shortening the bloom life to only about 7 days.

In another study, described in Example 5, the effect of ETR on bloom life was investigated for roses. The study was designed to measure the effect of ETR on bloom life when used in combination with aluminum sulfate, a traditional rose preservative. The protocol consisted of three steps. In the first step, upon receipt from the supplier, roses were cut to about 12 inches in length and were placed immediately in a "pulse solution" and maintained at room temperature for 3 h. Pulse solutions consisted of either 4 mM aluminum sulfate or 4 mM aluminum sulfate plus 1 mM ETR. After the 3 hour period, the roses were placed in a 4° C. cold room for 48 hours in the same pulse solutions. Following this 48 hour cooling step, the flowers were brought to room temperature, and groups of 10–12 individual flowers were placed in storage solutions containing various combinations of 4 mM aluminum sulfate, 1 mM ETR, a nutrient supplement (see Example 5) and, in one case, 0.08% citric acid with 0.04% sodium citrate. The results are shown in FIGS. 5A and 5B.

Figure 5A:
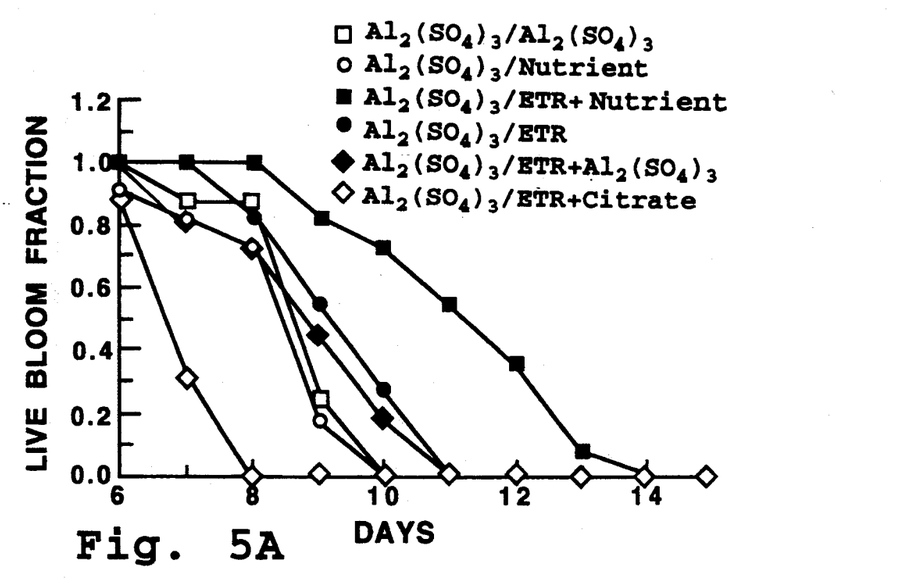
FIGS. 5A and 5B show time courses of live bloom fraction for roses treated first with a pulse solution (3 h at room temperature, then 48 h at 4° C.), followed by transfer to a storage solution at room temperature. The pulse solutions of FIG. 5A contain aluminum sulfate, whereas the pulse solutions of FIG. 5B additionally contain 1 mM 5-ethylthio-D-ribose (except for control samples).

FIG. 5A shows the time course of live bloom fraction of roses subjected to a pulse solution of 4 mM aluminum sulfate and various storage solutions as above. As can be seen, storage solutions containing ETR alone, ETR plus aluminum sulfate, aluminum sulfate alone, or nutrient supplement alone, all showed similar time courses, with the live bloom fraction beginning to decline on day 7 or 8 and dropping to zero by day 11. The best result was obtained with ETR plus nutrient supplement, where the bloom fraction didn't begin to decline until about day 9 and decreased steadily thereafter until day 14. ETR plus citric acid, however, gave a poor result, with the live bloom fraction having dropped to zero by day 8.

Figure 5B:
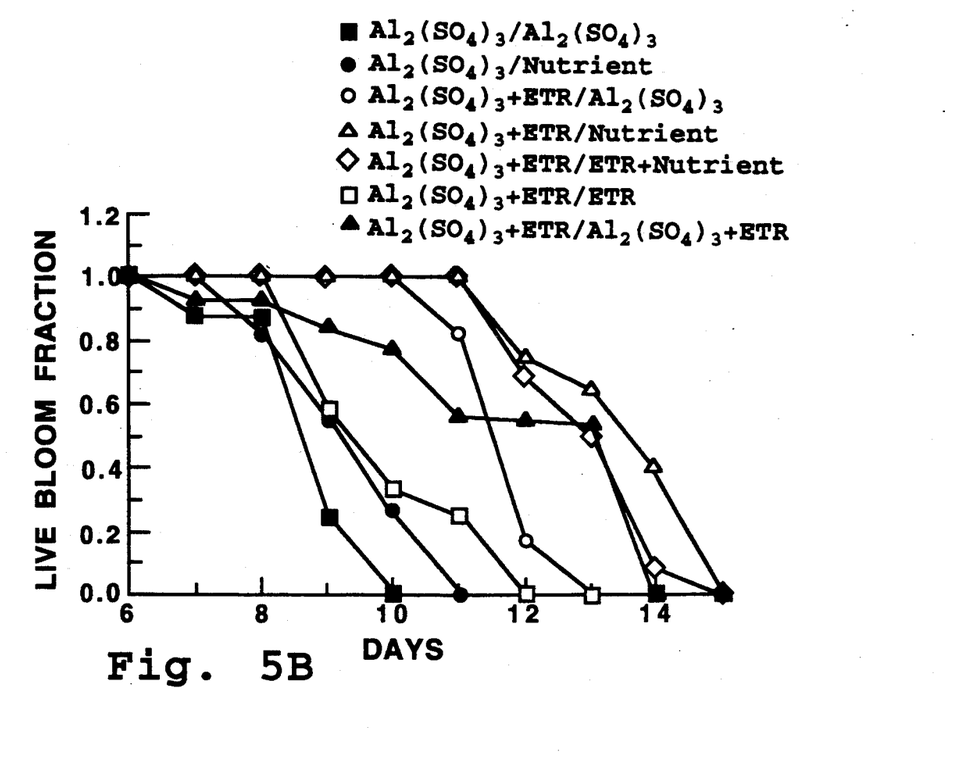

With reference to FIG. 5B, the inclusion of 1 mM ETR in all of the pulse solutions (except for two control solutions) enhanced bloom life in several instances. Specifically, the use of a pulse solution of aluminum sulfate and 1 mM ETR, followed by a storage solution of either aluminum sulfate, nutrient supplement, or nutrient supplement plus 1 mM ETR, delayed the onset of senescence by about 3 or 4 days relative to what was observed with the appropriate comparison samples in FIG. 5A, where ETR had been omitted from the pulse solution. Interestingly, use of a storage solution containing ETR together with aluminum sulfate afforded a result similar to that observed using a storage solution of aluminum sulfate alone, except that the decline in live bloom fraction was spread over a longer duration of time (from about day 7 to day 14). This result was still better than when the pulse solution and the storage solution both contained only aluminum sulfate.

The results from this study (FIGS. 5A and 5B) show that the inclusion of 1 mM ETR in a pulse solution of aluminum sulfate delayed the onset of senescence by up to 3 or 4 days, particularly when the storage solution contained nutrient supplement or aluminum sulfate.

It will be seen from the foregoing how various objects and features of the invention are met. The ETR compound is effective to extend the bloom life of cut flowers significantly. The concentrations of ETR required for bloom life extension are relatively low, e.g., in the 0.1 to 5 mM range. The ETR preservative is non-toxic to humans, and is thus advantageous over prior art preservatives such as silver thiosulfate. In addition, ETR and related 5-deoxy-5-alkylthioribose compounds can be synthesized easily and in high yield by a novel method of synthesis which also forms part of the invention.

The examples that follow below illustrate, but are not in any way intended to limit the scope of the invention.

EXAMPLES

NMR Spectra $^{13}C$ NMR spectra were obtained on a Bruker AMX-400 FT-NMR spectrometer at 100.62 MHz (for $^{13}C$) using proton decoupling. Spectra were measured in $CDCl_3$ in 5 mm tubes at room temperature and were referenced with respect to the $^{13}C$ signal of $CDCl_3$ (77.0 ppm).

Example 1

Synthesis of ETR

A. Methyl 2,3-O-isopropylidene-$\beta$-D-ribofuranoside (I).

A mixture of D-ribose (5 g), acetone (25 ml), methanol (25 ml) conc. $H_2SO_4$ (0.5 ml) and dry 3 Å molecular sieves (7 g) was refluxed with stirring for 20 h in a 100 ml flask. Following the first 20 hours of refluxing, additional portions of conc. $H_2SO_4$ (0.5 ml) and 3 Å molecular sieves (2.5 g) were added, and the resultant mixture was refluxed an additional 4 h. After cooling to room temperature, the reaction mixture was quickly neutralized with saturated $NaHCO_3$ (solid $NaHCO_3$ could also be used), and solvent was evaporated using a rotary evaporator. The resultant oil was taken up in chloroform and washed twice with saturated aqueous $NaHCO_3$, once with water, and once with saturated NaCl. The washed chloroform solution was dried over $MgSO_4$ and then evaporated to dryness, leaving an oily residue. High vacuum distillation (0.08 Torr, b.p. 90°–95° C.) yielded 5.23 g (77%) of I as a clear, colorless oil. TLC (silica; ethyl acetate): $R_f$ 0.52 (I), 0.13 (ribose). Visualization spray reagent: saturated ceric sulfate in 65% sulfuric acid. TLC plates were sprayed and heated until dark brown spots appeared.

B. Methyl 2,3-O-isopropylidine-5-O-p-toluenesulfonyl-$\beta$-D-ribofuranoside (II).

To a chilled solution of methyl 2,3-O-isopropylidene-$\beta$-D-ribofuranoside (II) (64.4 g) in triethylamine (47.7 g; distilled from $CaH_2$) and dichloromethane (200 ml) was added p-toluenesulfonyl chloride (66.2 g), and the resultant mixture was refluxed with stirring under nitrogen atmosphere for 20 h. After cooling to room temperature, 50 ml of saturated aqueous $NaHCO_3$ was added and stirred for 10 min. After stirring was stopped, the reaction mixture separated into a lower, amber-colored (dichloromethane) layer and an upper, milky-white (aqueous) layer. The dichloromethane layer was separated and washed twice with 100 ml of saturated aqueous $NaHCO_3$. The aqueous washings were combined and washed once with 100 ml of dichloromethane. The combined organic extracts were washed once with saturated aqueous NaCl, dried over $MgSO_4$, and then evaporated to a white solid. Recrystallization from ethyl acetate-hexane yielded 74 g of (II) as white crystals (65%), m.p. 80°–84° C. in the first crop, and 8 g of slightly impure solid in a second crop. TLC (silica; 25% ethyl acetate in hexane): $R_f$ 0.26 (II). Ceric sulfate/sulfuric acid visualization spray as in A above.

C. Methyl 5-deoxy-5-ethylthio-2,3-O-isopropylidene-$\beta$-D-ribofuranoside (III).

A solution of ethanethiol (11.5 ml, 155 mmol) in 1N sodium methoxide in methanol (150 ml, 150 mmol sodium methoxide) was added to a solution of methyl 2,3-O-isopropylidene-5-O-p-toluenesulfonyl-$\beta$-D-ribofuranoside (50 g, 140 mmol in 200 ml dry methanol) and heated at reflux for 24 h. Solvents were removed by evaporation in vacuo, and the sticky residue was taken up in diethyl ether (300 ml) and washed with water (4×100 ml). The ether phase was dried and concentrated in vacuo to furnish a viscous oil. Fractional distillation (70° C. at 0.06 Torr) using a short-path distillation apparatus afforded 30.0 g (86.5% yield) of methyl 5-deoxy-5-ethylthio2,3-O-isopropylidene-$\beta$-D-ribofuranoside (III) as a colorless, viscous oil. TLC (silica; 25% ethylacetate in hexane): $R_f$ 0.44 (III); visualization spray as in A above.

D. 5-Deoxy-5-ethylthio-D-ribose (IV).

A solution of methyl 5-deoxy-5-ethylthio-2,3-O-isopropylidene-$\beta$-D-ribofuranoside (3.0 g, 20 mmol) in peroxide-free dioxane (25 ml), water (25 ml), and 25 ml (packed volume) of Dowex-50-X2 (100–200 mesh, H+ form) were stirred for 5 h at 60° C. The mixture was then filtered and evaporated in vacuo. The resulting oil was taken up in water (50 ml), decolorized with activated charcoal (3 g), filtered through a layer of Celite, and re-evaporated in vacuo to furnish 5-deoxy-5-ethylthio-D-ribofuranose (IV) as a nearly colorless syrup. Purity was estimated to be greater than 95% by TLC (100% ethylacetate, $R_f$ 0.32). Proton decoupled $^{13}C$-NMR (solvent and internal standard=CDCl3, 77.0 ppm): $\delta$(ppm) 101.5 (C-1$\beta$), 96.5 (C-1$\alpha$), 82.4 (C-4$\alpha$), 81.8 (C-4$\beta$), 75.9 (C-2$\beta$), 74.1 (C-3$\beta$), 73.3 (C-3$\alpha$), 71.2 (C-2$\alpha$), 35.7 (C-5$\beta$), 34.5 (C-5$\alpha$), 26.9 (C-6$\alpha$), 26.7 (C-6$\beta$) and 15.0 (C-7$\alpha$,$\beta$). $^{13}C$-NMR assignments were based on the known assignments for $\alpha$- and $\beta$-D-ribofuranose.

Example 2

Comparison of Effects of ETR and Silver Thiosulfate on the Bloom Life of Carnations Whole fresh-cut carnations (Dianthus caryophyllus L., Katia and Vanessa varieties) were obtained from Mazzanti Carnations, Inc. (South San Francisco, Calif.) and were shipped to the Agritope laboratory in Beaverton, Oreg., by overnight air freight. Prior to shipment, groups of flowers were treated by bathing the stems for 24 hours in a solution of (a) water alone, (b) 5 mM ETR in water, or (c) an aqueous STS (silver thiosulfate) solution such as typically used in the flower industry. The flowers were removed from the solutions just before shipment.

Upon arrival, the flower stems were cut to about 12 inches in length and, as groups of 6, were placed in one of several storage solutions for storage at 22°±2° C. under cool-white fluorescent lights in a well ventilated room. Storage solutions were replenished daily. The bloom life of a given flower was recorded as the last day the flower had an acceptable bloom, as defined in the "Definitions" section above. The results, reported as an average for the six flowers in each group, are shown in Table 1. Note that the large standard deviations for some of the measured values reflects the variability in the study.

Example 3

Comparison of Effects of ETR and Silver Thiosulfate on Ethylene Production by Carnations Carnations, pretreated as in Example 2 with a solution of either water alone or 5 mM ETR in water, were weighed, placed individually in separate vials containing 10 ml of either water or 2 mM ETR in water, and then transferred with their respective vials to quart mason jars with the lids removed. Ethylene evolution was assayed daily by sealing each jar for about 1 hour and then removing a 2 ml aliquot for gas chromatographic (GC) analysis. GC analysis was performed using a Hewlett Packard 5890 gas chromatograph equipped with a flame ionization detector and a 6 ft Porapak column as described by Ward et al. (1978). Data from the flame ionization detector were recorded using a Hewlett Packard Vectra computer running the current version of the Hewlett Packard "ChemStation" program, allowing measurements of ethylene as low as about 0.1 nL in a 2 ml sample (~0.05 ppm). Ethylene production values were recorded in units of (nL of ethylene/gram)/hour, where the weight of the flower had been measured in grams. The results are shown in FIGS. 2A-2C, with each trace representing a time course for a separate flower.

Example 4

Effect of MTR Analogs on Bloom Life of Carnations

Carnations (Nora, Katia, Tanga, and Vanessa varieties) were obtained from Mazzanti Carnations, Inc. (South San Francisco, Calif.). Following a 24 hour hydration step in water immediately after harvest, the carnations were shipped to the Agritope laboratory in Beaverton, Oreg., by overnight air freight. Three flowers of each variety were then placed in either water, a nutrient solution ("Externe", a low-pH high-sugar solution supplied by Agrimax, Inc., St. Paul, Minn.), or the nutrient solution additionally containing a 1 mM concentration of one of the compounds shown in FIG. 3.

The combined results for the four varieties tested are shown in FIG. 4.

Example 5

Effect of ETR On Bloom Life of Roses

Roses (Samantha variety) were obtained from the greenhouses of Oregon Rose, Inc., in Hillsboro, Oreg. To investigate the effect of ETR on bloom life, roses were subjected to a three step protocol. In the first step, upon receipt from the supplier, the roses were cut to about 12 inches in length and were immediately placed in a pulse solution and maintained at room temperature for 3 h. Pulse solutions consisted of either 4 mM aluminum sulfate or 4 mM aluminum sulfate plus 1 mM ETR. After the 3 hour period, the roses were placed in a 4° C. cold room for 48 hours in the same pulse solutions. At the end of the 48 hour period, the flowers were brought to room temperature, and groups of 10-12 individual flowers were placed in storage solutions containing various combinations of 4 mM aluminum sulfate, 1 mM ETR, a nutrient supplement ("Externe", as in Example 4), and in one case, 0.08% citric acid with 0.04% sodium citrate. The flowers were monitored daily to determine the bloom life of each flower. The bloom life was defined as the last day the flower had an acceptable bloom, as defined in the "Definitions" section above. The results are shown in FIGS. 5A and 5B.

Although the invention has been described with respect to particular embodiments, it will be appreciated that various changes and modifications can be made without departing from the invention.

It is claimed:

1. A method of extending bloom life of a cut flower comprising
providing a storage solution containing 5-deoxy-5-ethylthio-D-ribose, and
bathing the stem of a cut flower in the solution.
2. The method of claim 1, wherein the concentration of 5-deoxy-5-ethylthio-D-ribose in the storage solution is from about 0.1 mM to 5 mM.
3. The method of claim 1, wherein said bathing is initiated immediately after harvesting the cut flower.
4. The method of claim 1, wherein the flower is a carnation, and the concentration of 5-deoxy-5-ethylthio-D-ribose in the storage solution is from about 1 mM to 5 mM.
5. The method of claim 1, wherein the flower is a rose, and the concentration of 5-deoxy-5-ethylthio-D-ribose in the storage solution is from about 0.1 mM to 1 mM.

* * * * *